United States Patent [19]

Lotti

[11] Patent Number: 5,153,205
[45] Date of Patent: Oct. 6, 1992

[54] METHOD TO REDUCE INTROACULAR PRESSURE WITHOUT CAUSING MIOSIS

[75] Inventor: Victor J. Lotti, Harleysville, Pa.

[73] Assignee: Merck & Co., Inc., Rahway, N.J.

[21] Appl. No.: 590,860

[22] Filed: Oct. 1, 1990

[51] Int. Cl.⁵ ............... A61K 31/445; A61K 31/415; A61K 31/495

[52] U.S. Cl. .................. 514/317; 514/255; 514/315; 514/397; 514/63

[58] Field of Search ............... 514/290, 315, 396, 317, 514/397, 255, 63

[56] References Cited

PUBLICATIONS

Invest Ophthamol Vis Sci., Jul. (1990), 31 pp. 1332–1338, Liu et al.
The Merck Index, Tenth Edition, 1983.
*Ann. Rev. Pharmacol. and Toxicol.*, George, R., Okun, R., Cho, A., eds. 26, pp. 401–426 (1986).
*Glaucoma: Applied Pharmacol. in Med. Treatment*, Drance, S., Neufeld, A., eds., pp. 357–393 (1984).
Doods, et al., *J. Pharmacol. and Experim. Therapeutics*, 242 No. 1, pp. 257–262 (1987).
Zimmerman, et al., *Opthalmology*, 89 No. 1, pp. 76–80 Jan. 1982.

Primary Examiner—Frederick E. Waddell
Assistant Examiner—Zohreh A. Fay
Attorney, Agent, or Firm—Carol S. Quagliato; Joseph F. DiPrima; William H. Nicholson

[57] ABSTRACT

Topical administration of a cholinomimetic agent, such as pilocarpine, in combination with a cholinergic $M_3$ receptor antagonist, such as 4-diphenyl-acetoxy-N-methylpiperidine, to the eye of a mammal reduces intraocular pressure without the concommitant miotic effect that normally occurs with administration of a cholinomimetic agent along.

23 Claims, 2 Drawing Sheets

METHOD TO REDUCE INTROACULAR PRESSURE WITHOUT CAUSING MIOSIS

BACKGROUND OF THE INVENTION

This invention relates to a method of reducing intraocular pressure (IOP) and treating glaucoma in mammals. More specifically, a combination of a cholinergic receptor agonist, also referred to as a cholinomimetic agent, such as pilocarpine, and a cholinergic $M_3$ receptor antagonist, such as 4-diphenyl-acetoxy-N-methylpiperidine (4-DAMP), topically applied to the eye of a mammal, can be used to reduce elevated IOP without causing the miotic effect that normally accompanies administration of a cholinomimetic agent alone.

Glaucoma refers to a group of diseases of the eye which are characterized by abnormally high intraocular pressure. The outer shell of the eyeball is made up of three coats: a tough outer fibrous tunic composed of variously arranged connective tissue fibers, the uveal tunic and the retina. The choroid is the posterior segment of the uveal tunic. The anterior part of the uvea, in part, is referred to as the ciliary body and is lined with two epithelial cell layers which secrete the aqueous humor which fills the anterior chamber of the eye. In a healthy eye the humor flows from the ciliary body through the pupil into the anterior chamber of the eye and leaves the eye through Schlemm's canal. The rate of formation and the rate of exit of this aqueous humor determines the intraocular pressure in the eyeball.

In subjects suffering from glaucoma the rate of elimination of aqueous humor from the eye is reduced which results in fluid build up within the eye and increased intraocular pressure. If high intraocular pressure is allowed to continue untreated it interferes with the blood supply to the nerve fibers of the retina and optic nerve and if left uncorrected the optic nerve dies and blindness results.

Glaucoma can be treated both through surgery or therapeutically with drugs. Surgery seeks to create new outlets for the aqueous humor and thereby reduce the intraocular pressure. A number of drugs have been discovered which, when either taken internally or applied topically to the eye, lower intraocular pressure but many are toxic and cause undesirable side effects, especially when used as chronic therapy.

Cholinomimetic agents, as exemplified by pilocarpine, are useful antiglaucoma agents which lower IOP by increasing aqueous humor outflow facility. However, their use is associated with numerous side effects, of which miosis and accommodation are the most serious. Zimmerman, T. J. and Wheeler, T. M., Miotics: Side Effects and Ways to Avoid Them, *Ophthalmology* 89: 76 (1982). A drug or drug combination which acted by a similar mechanism of action as pilocarpine but which did not cause miosis would represent a significant advance in the treatment of glaucoma.

Now with the present invention there is provided a novel method of treatment for elevated IOP which allows a cholinomimetic agent such as pilocarpine to be used to lower IOP without an accompanying miotic effect. The novel method of this invention comprises topical administration of a cholinergic $M_3$ receptor antagonist, such as 4-DAMP, in combination with a cholinomimetic agent to the eye of a mammal in need of such treatment.

It is generally agreed on the basis of pharmacological studies that cholinergic muscarinic receptors exist in a variety of subtypes. Mitchelson, F., Muscarinic Receptor Differentiation, *Pharmacol. Ther.* 37: 357 (1988). The cholinergic antagonist 4-DAMP has been shown to selectively block the $M_3$ (also known as $M_2$ beta or $M_2$ glandular) receptor subtype in in vivo studies. Doods, H. N., et al., Selectivity of Muscarinic Antagonists in Radioligand and in Vivo Experiments for the Putative $M_1$, $M_2$ and $M_3$ Receptors, *J. Pharmacol. Exp. Ther.* 242: 257–262 (1987). The terms "cholinergic $M_3$ receptor antagonist" and "$M_3$ antagonist" have the same meaning and will be used interchangeably herein.

When administered alone to the eye of an African Green monkey with elevated IOP, 4-DAMP causes mydriasis of the pupil as shown in FIG. 2, but has no appreciable effect on IOP, as shown in FIG. 1. Administration of pilocarpine alone produces a reduction in IOP FIG. 1), accompanied by a profound miosis (FIG. 2). However, when 4-DAMP is instilled in the eye one hour prior to pilocarpine administration, the 4-DAMP completely prevents the miotic effect of pilocarpine (FIG. 2) without affecting pilocarpine's action upon IOP (FIG. 1).

DETAILED DESCRIPTION OF INVENTION

Figure 1:
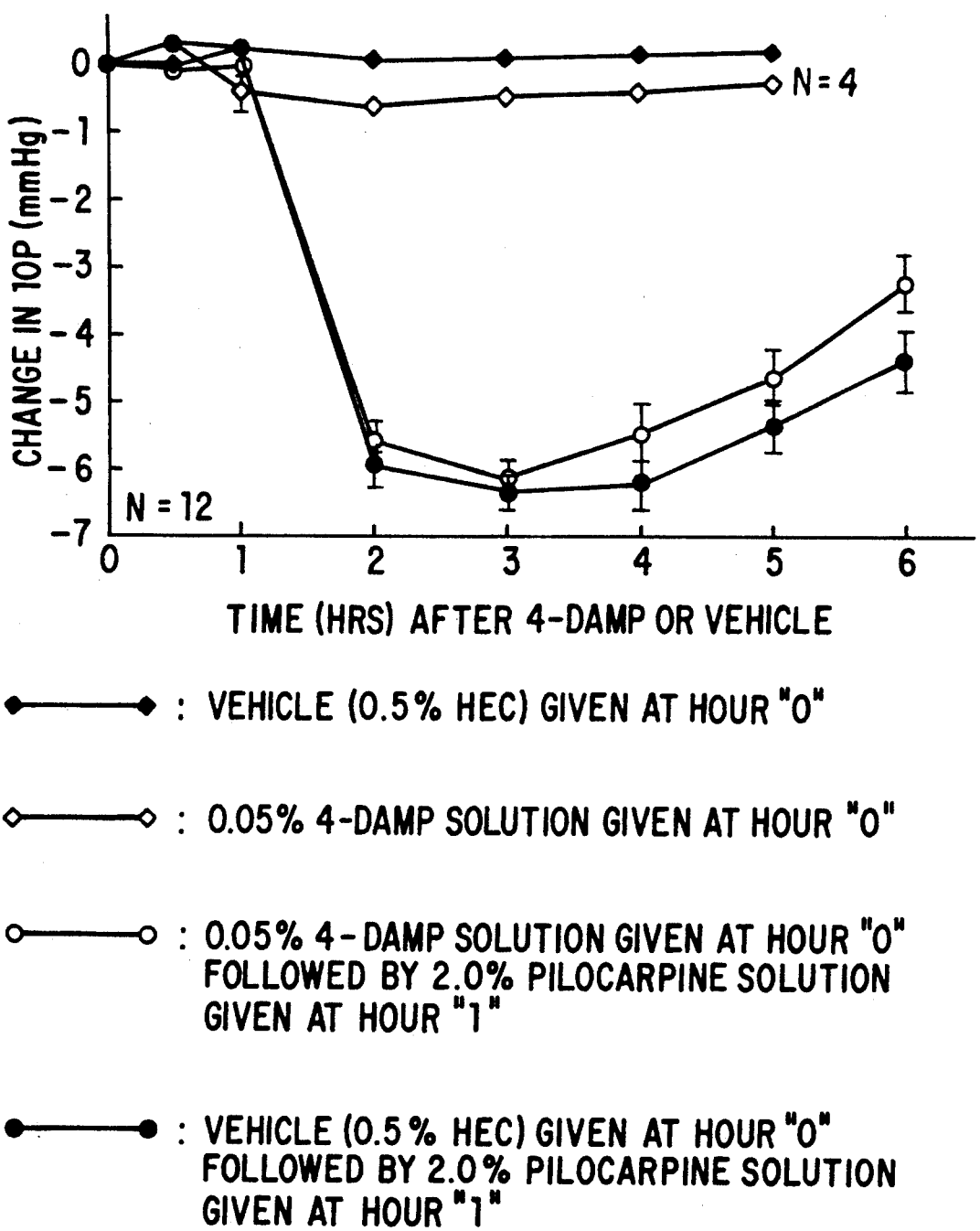
FIG. 1 shows the effect of 4-DAMP upon the ocular hypotensive action of pilocarpine in African Green monkeys over a period of six hours.

The novel method of this invention involves the combined topical administration of a cholinomimetic agent and a cholinergic $M_3$ receptor antagonist to the eye of a mammal suffering from elevated intraocular pressure in order to reduce the intraocular pressure without causing the concomitant miotic effect that normally accompanies administration of a cholinomimetic agent alone.

The purpose of administering the cholinomimetic agent to the eye is to reduce the IOP, the primary goal of treatment. Cholinomimetic agents that may be used in the method of this invention include pilocarpine, carbachol, methacholine and the pharmaceutically acceptable salts thereof. The preferred cholinomimetic agent to be used in combination with a cholinergic $M_3$ receptor antagonist is pilocarpine.

Administration of the cholinergic $M_3$ receptor antagonist in combination with the cholinomimetic agent is necessary to essentially eliminate the miotic effect induced by the application of the cholinomimetic agent alone. Cholinergic $M_3$ receptor antagonists that may be used in the method of this invention include 4-DAMP, hexahydrosiladifenidol, p-fluorohexahydrosiladifenidol, hexocyclium, silahexocyclium, fluorohexbutinol, and the pharmaceutically acceptable salts thereof. The preferred cholinergic $M_3$ receptor antagonist to be used in combination with a cholinomimetic agent is 4-DAMP. The preferred combination of compounds for treatment of glaucoma and elevated IOP is pilocarpine and 4-DAMP.

The $M_3$ antagonist should be applied topically to the eye of the patient (animal or human) in need of treatment concurrently with or up to about 120 minutes prior to application of the cholinomimetic agent. Preferably, the $M_3$ antagonist should be applied concurrently with or up to about 60 minutes prior to cholinomimetic agent application.

The M₃ antagonist and the cholinomimetic agent can be administered to patients in need of such treatment in topical ocular formulations in the form of solutions, ointments, inserts, gels and the like. The M₃ antagonist and the cholinomimetic agent can each be in a separate formulation or the two compounds may be combined in a single formulation for topical ocular administration.

The pharmaceutical formulation of the cholinomimetic agent and the pharmaceutical formulation of the M₃ antagonist would each typically contain from about 0.01% to 15% by weight of the respective compounds, and preferably between 0.05% and 4%. Most preferably, the pharmaceutical formulation of the cholinomimetic agent would contain about 2.0% by weight of the cholinomimetic agent, and the pharmaceutical formulation of the M₃ antagonist would contain about 0.05% of the M₃ antagonist.

A pharmacuetical formulation containing both the cholinomimetic agent and the M₃ antagonist would typically contain from about 0.01% to 15% by weight of each of the respective compounds, and preferably between 0.05% and 4%. Most preferably, the formulation would contain about 2.0% by weight of the cholinomimetic agent and about 0.05% by weight of the M₃ antagonist.

The compounds employed in this invention can be administered to patients in need of such treatment in dosage combinations that will provide optimal pharmaceutical efficacy. Although the doses may vary from patient to patient depending upon the severity of the disease and other factors recognized by those skilled in the art, the dosage range will generally be about 0.01 mg. to 15 mg. of the cholinomimetic agent, preferably between 0.5 mg. and 6 mg., and about 0.01 mg. to 2 mg. of the cholinergic M₃ receptor antagonist, preferably 0.05 mg. to 0.5 mg.

The dosage amount of M₃ antagonist necessary to prevent miosis is dependant upon the dosage amount of cholinomimetic agent used to treat the patient. A weight ratio of cholinomimetic agent to M₃ antagonist of from about 80:1 to 1:1 can be used, preferably between 50:1 and 30:1, and most preferably 40:1.

The following example is given for the purpose of illustrating the present invention and should not be construed as being a limitation on the scope or spirit of the instant invention.

EXAMPLE 1

Figure 2:
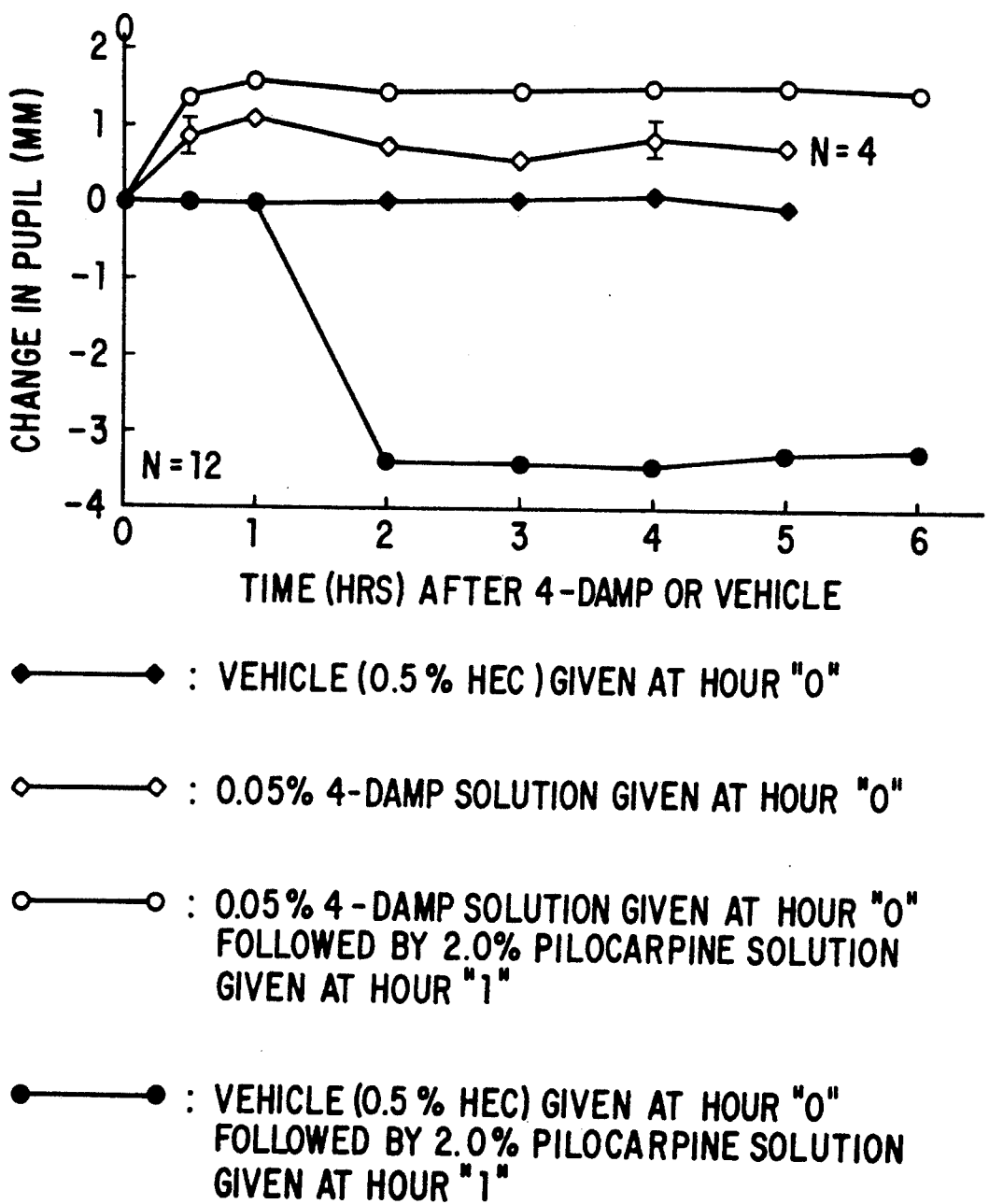
FIG. 2 shows the effect of 4-DAMP upon the miotic action of pilocarpine in African Green monkeys over a period of six hours.

Male or female African Green monkeys (2.0–4.5 kg) were fasted following their afternoon feeding on the day prior to the experiment. The monkeys were anesthetized in their cages with approximately 10 mg/kg i.m. ketamine HCl (Vetalar® or Ketaset®). Once sedated, the animals were restrained in monkey chairs and brought to the laboratory. One drop of 0.5% proparacaine HCl (Ophthetic®) was instilled into each eye. After 30 seconds, intraocular pressure and pupil size determinations were taken in each eye (control or "0" time reading) using a Digilab Modular One® Pneuma Tonometer and millimeter ruler, respectively. Both eyes were then flushed with saline. Next either 25 μl of vehicle (0.5% hydroxyethylcellulose or HEC) or 25 μl of test agent (0.05% solution of 4-DAMP in 0.5% HEC) was administered into the cul-de-sac of both eyes. Then, either 25 μl of pilocarpine (2.0% solution of pilocarpine in 0.5% HEC) was administered into the cul-de-sac of both eyes one hour after vehicle or test agent administration, or no pilocarpine was administered. The IOP and pupil size were determined at the same time at the intervals indicated in FIGS. 1 and 2. Supplemental doses of 10 mg/animal i.m. ketamine HCl were given 3–5 minutes prior to each IOP determination. Proparacaine HCl (0.5%) (one drop/eye) was also instilled immediately prior to IOP determinations. Following the final IOP determination, both eyes were flushed liberally with saline and a sterile ophthalmic ointment (Ilotycin®, erythromycin, 5 mg/gm) was applied. At least 3 days separated individual intraocular pressure experiments.

The following examples of ophthalmic formulations are given by way of illustration.

EXAMPLE 2

| Pilocarpine | 20 mg |
| --- | --- |
| 4-DAMP | 0.5 mg |
| Monobasic sodium phosphate 2H₂O | 0.5 mg |
| Dibasic sodium phosphate 12H₂O | 19.7 mg |
| Benzalkonium chloride | 0.10 mg |
| Water for injection q.s. ad. | 1.0 ml |

The pilocarpine and 4-DAMP, phosphate buffer salts and benzalkonium chloride are added to and dissolved in water. The pH of the composition is adjusted to 6.8 and diluted to volume. The composition is rendered sterile by sterile filtration.

EXAMPLE 3

| Pilocarpine | 20 mg |
| --- | --- |
| 4-DAMP | 0.5 mg |
| petrolatum q.s. ad. | 1 gram |

The compounds and the petrolatum are aseptically combined.

What is claimed is:

1. A method of reducing intraocular pressure in mammals which comprises topically applying to the eye a combination of (a) a therapeutically effective amount of a cholinergic M₃ receptor antagonist selected from the group consisting of 4-diphenyl-acetoxy-N-methyl-piperidine, hexahydrosiladifenidol, p-fluorohexahydrosiladifenidol, hexocyclium, silahexocyclium, fluorohexbutinol, and the pharmaceutically acceptable salts thereof, concurrently with or followed by (b) a therapeutically effective amount of a cholinomimetic agent selected from the group consisting of pilocarpine, carbachol, methacholine, and the pharmaceutically acceptable salts thereof, whereby intraocular pressure is reduced with essentially no miotic effect.

2. The method of claim 1 wherein the cholinergic M₃ receptor antagonist is 4-diphenyl-acetoxy-N-methyl-piperidine or a pharmaceutically acceptable salt thereof.

3. The method of claim 1 wherein the cholinomimetic agent is pilocarpine or a pharmaceutically acceptable salt thereof.

4. The method of claim 3 wherein the cholinergic M₃ receptor antagonist is 4-diphenyl-acetoxy-N-methyl-piperidine or a pharmaceutically acceptable salt thereof.

5. The method of claim 1 wherein the cholinergic M₃ receptor antagonist is applied concurrently with or up to about 120 minutes prior to cholinomimetic agent application.

6. The method of claim 5 wherein the cholinergic $M_3$ receptor antagonist is applied concurrently with or up to about 60 minutes prior to cholinomimetic agent application.

7. The method of claim 2 wherein the amount of 4-diphenyl-acetoxy-N-methylpiperidine is from about 0.01% to 15% by weight in an aqueous formulation.

8. The method of claim 7 wherein the amount of 4-diphenyl-acetoxy-N-methylpiperidine is about 0.05% by weight.

9. The method of claim 3 wherein the amount of pilocarpine is from about 0.01% to 15% by weight in an aqueous formulation.

10. The method of claim 9 wherein the amount of pilocarpine is about 2.0% by weight.

11. The method of claim 2 wherein the dosage amount of 4-diphenyl-acetoxy-N-methylpiperidine is from about 0.01 mg. to about 2 mg.

12. The method of claim 11 wherein the dosage amount of 4-diphenyl-acetoxy-N-methylpiperidine is from about 0.05 mg. to about 0.5 mg.

13. The method of claim 3 wherein the dosage amount of pilocarpine is from about 0.01 mg. to about 15 mg.

14. The method of claim 13 wherein the dosage amount of pilocarpine is from about 0.5 mg. to about 6 mg.

15. The method of claim 4 wherein the weight ratio of pilocarpine to 4-diphenyl-acetoxy-N-methylpiperidine applied is from about 80:1 to 1:1.

16. The method of claim 15 wherein the weight ratio of pilocarpine to 4-diphenyl-acetoxy-N-methylpiperidine applied is from about 50:1 to 30:1.

17. The method of claim 16 wherein the weight ratio of pilocarpine to 4-diphenyl-acetoxy-N-methylpiperidine applied is about 40:1.

18. An opthalmic formulation comprising a therapeutically effective amount of a cholinomimetic agent selected from the group consisting of pilocarpine, carbachol, methacholine, and the pharmaceutically acceptable salts thereof, a therapeutically effective amount of a cholinergic $M_3$ receptor antagonist selected from the group consisting of 4-diphenyl-acetoxy-N-methylpiperidine, hexahydrosiladifenidol, p-fluorohexahydrosiladifenidol, hexocyclium, silahexocyclium, fluorohexbutinol, and the pharmaceutically acceptable salts thereof, and an opthalomogically acceptable carrier.

19. The formulation of claim 18 wherein the cholinomimetic agent is pilocarpine.

20. The formulation of claim 18 wherein the cholinergic $M_3$ receptor antagonist is 4-diphenyl-acetoxy-N-methylpiperidine.

21. The formulation of claim 19 wherein the cholinergic $M_3$ receptor antagonist is 4-diphenyl-acetoxy-N-methylpiperidine.

22. The formulation of claim 21 wherein the percent weight of 4-diphenyl-acetoxy-N-methylpiperidine is 0.05%.

23. The formulation of claim 22 wherein the percent weight of pilocarpine is 2.0%.

* * * * *